US012379262B2

(12) United States Patent
Takagi et al.

(10) Patent No.: US 12,379,262 B2
(45) Date of Patent: Aug. 5, 2025

(54) TEMPERATURE RISE EVALUATION APPARATUS

(71) Applicants: National Institute of Advanced Industrial Science and Technology, Tokyo (JP); Otsuka Medical Devices Co., Ltd., Tokyo (JP)

(72) Inventors: Ryo Takagi, Ibaraki (JP); Koji Inui, Tokyo (JP)

(73) Assignees: National Institute of Advanced Industrial Science and Technology, Tokyo (JP); Otsuka Medical Devices Co., Ltd., Tokyo (JP)

( * ) Notice: Subject to any disclaimer, the term of this patent is extended or adjusted under 35 U.S.C. 154(b) by 105 days.

(21) Appl. No.: 18/558,120

(22) PCT Filed: Apr. 19, 2022

(86) PCT No.: PCT/JP2022/018150
§ 371 (c)(1),
(2) Date: Oct. 30, 2023

(87) PCT Pub. No.: WO2022/230719
PCT Pub. Date: Nov. 3, 2022

(65) Prior Publication Data
US 2024/0210256 A1    Jun. 27, 2024

(30) Foreign Application Priority Data

Apr. 30, 2021 (JP) ................................ 2021-077837

(51) Int. Cl.
*A61N 7/00* (2006.01)
*A61N 7/02* (2006.01)
*G01K 11/12* (2021.01)

(52) U.S. Cl.
CPC .............. *G01K 11/12* (2013.01); *A61N 7/02* (2013.01)

(58) Field of Classification Search
CPC ........... A61N 7/02; G01K 11/12; G01K 15/00
See application file for complete search history.

(56) References Cited

FOREIGN PATENT DOCUMENTS

| JP | S649328 A | 1/1989 |
| JP | 2006010320 A | 1/2006 |
| WO | 2021065800 A1 | 4/2021 |

OTHER PUBLICATIONS

International Search Report, dated Jun. 28, 2022, 2 pages, received in International Application No. PCT/JP2022/018150.

(Continued)

*Primary Examiner* — Mark D Remaly
(74) *Attorney, Agent, or Firm* — AVEK IP, LLC

(57) ABSTRACT

A system for evaluating a treatment device capable of radiating ultrasound for cauterizing human tissue, the system including: simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged; a light source radiating planar light from the whole circumference, the light source being arranged surrounding the simulated tissue; an image taking device taking cross-sectional color images of light irradiation surfaces of the simulated tissue; and movement mechanisms causing the light source and the image taking device to relatively move in a photographing axis direction of the image taking device relative to the simulated tissue; and a movement mechanism control/information processing unit controlling the movement mechanism.

15 Claims, 15 Drawing Sheets

(56) References Cited

OTHER PUBLICATIONS

T. Iwahashi et al., Visualization of Temperature Distribution around Focal Area and Near Fields of HighIntensity Focused Ultrasound Using a 3D Measurement System, Advanced Biomedical Engineering, 2018, pp. 1-7, vol. 7, Japan.

Fig. 7
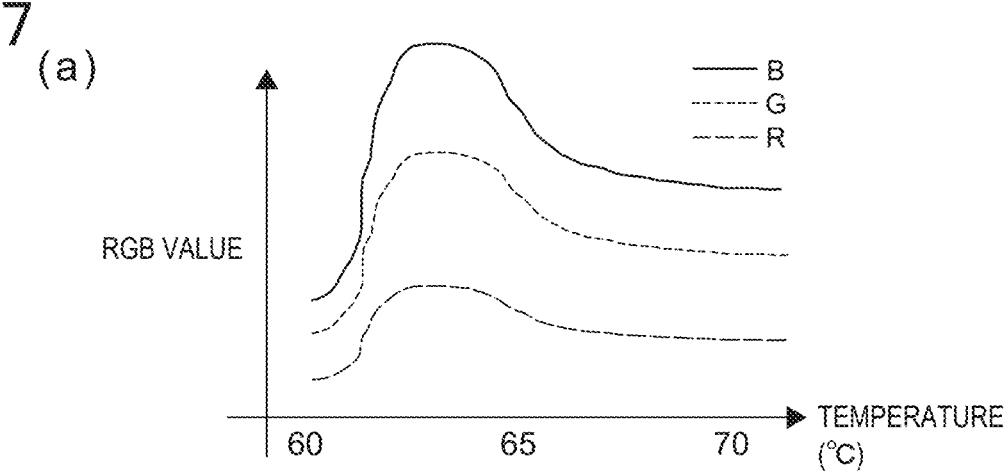
(a)
PRIMARY COMPONENT ANALYSIS
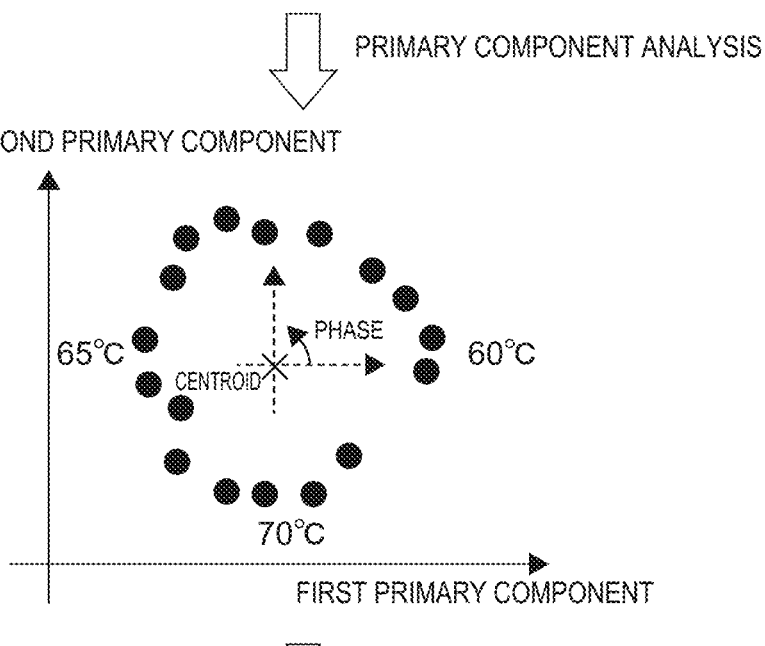
(b)
COLOR-TEMPERATURE CONVERSION TABLE
(c)
| PHASE | TEMPERATURE |
|---|---|
| 0° | 60°C |
| 0.2° | 60.2°C |
| ... | ... |
| ... | ... |
| ... | ... |
| ... | ... |
| 279° | 70°C |

Fig. 9
T = 1.6s 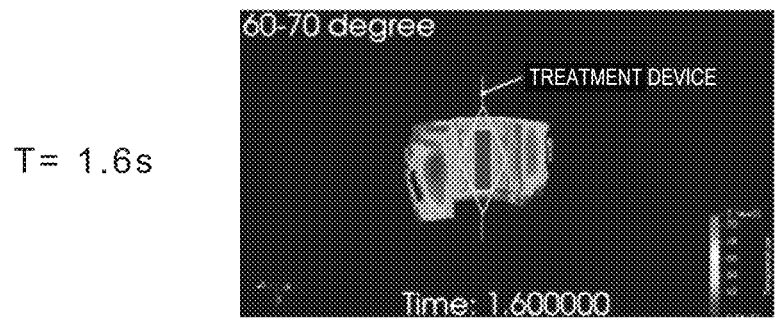
T = 3.7s 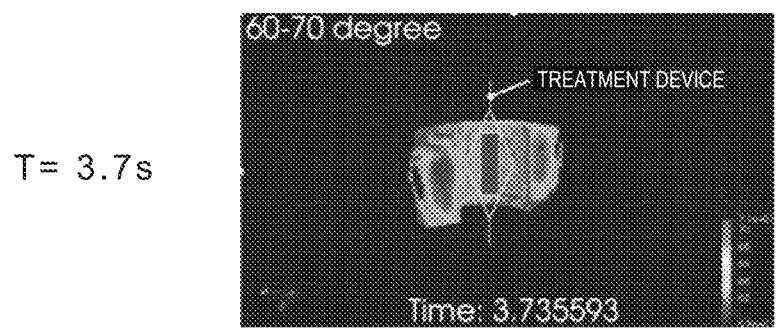
T = 14.4s 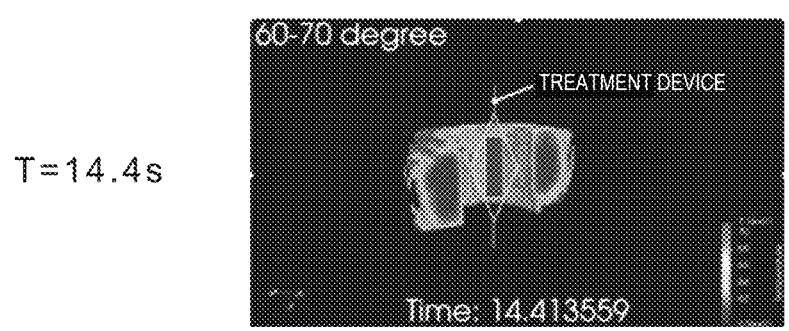
T = 29.3s 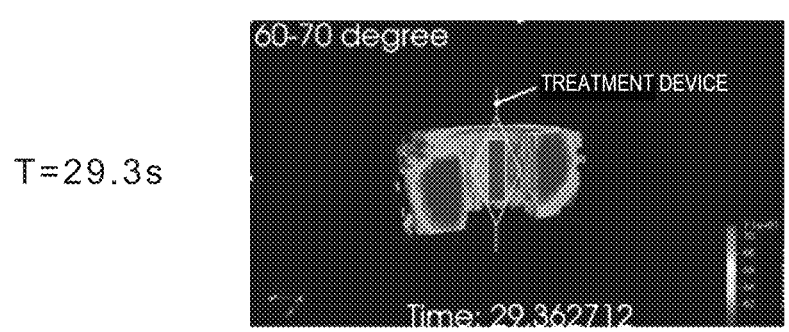

Fig. 13

| COLOR-TEMPERATURE CONVERSION TABLE 1 (cal1) ||
|---|---|
| PHASE | TEMPERATURE |
| 0° | 60°C |
| 0.34° | 60.2°C |
| ... | ... |
| ... | ... |
| ... | ... |
| ... | ... |
| 267° | 69.9°C |

| COLOR-TEMPERATURE CONVERSION TABLE 2 (cal2) ||
|---|---|
| PHASE | TEMPERATURE |
| 0° | 60°C |
| 0.50° | 60.8°C |
| ... | ... |
| ... | ... |
| ... | ... |
| ... | ... |
| 278.9° | 70.2°C |

TEMPERATURE RISE EVALUATION APPARATUS

CROSS-REFERENCE TO RELATED APPLICATIONS

This application is the U.S. national phase of, and claims priority to, International Application No. PCT/JP2022/018150, filed Apr. 19, 2022, which designated the U.S., and which claims priority to Japanese Patent Application No. 2021-077837, filed Apr. 30, 2021.

FIELD OF THE DISCLOSURE

The present invention relates to a temperature rise evaluation apparatus.

BACKGROUND

Recently, as one of dynamic hypertension treatment methods, catheter treatment referred to as renal sympathetic denervation (RDN) has been attracting attention. It is known that, when activity of sympathetic nerves around a kidney increases, vasoconstriction and the like are caused, and increase in blood pressure is caused. The RDN is a treatment method of, with sympathetic nerves around a kidney as a target of cauterization, suppressing the function of the sympathetic nerves to reduce increase in blood pressure. RF treatment of cauterizing sympathetic nerves while directly cauterizing blood vessel walls mainly by an electrode as cauterization means, ultrasonic treatment of cauterizing only sympathetic nerves within a range of approximately 5 mm outside a blood vessel diameter by an ultrasonic device without directly damaging blood vessel walls, and the like are exemplified. In a device evaluation method at the time of development and clinical application of a device for the above, one of problems is that there is not a method for automatically and easily visualizing temperature rise around blood vessels cauterized by the device. If temperature rise in a three-dimensional space around blood vessels can be easily measured, it can be expected that it leads to finding of breakage, defects, and the like of a device in three-dimensional (XYZ) space at the time of development and clinical application. Further, in development of a new device, it can be expected that the method can be applied as a device evaluation method for optimizing temperature rise of tissue outside a blood vessel diameter. As a prior-art technique, it is possible to, by three-dimensionally performing scan measurement in an ultrasonic sound field caused by a device, using a hydrophone (an ultrasonic sensor) or the like, measure three-dimensional sound field distribution by the device, but it is not possible to actually measure temperature rise in an actual living body or of a phantom simulating a living body.

Further, there is a prior-art technique of inserting a thermocouple into a living body phantom to directly evaluate temperature rise. However, the measurement is basically measurement at a finite point, and it is difficult to measure temperature of all points inside a living body and the living body phantom in three-dimensional space (for example, length×width×depth=approximately 50 mm×50 mm×50 mm). There is also a fear that the ultrasonic sound field is disturbed by insertion of the thermocouple. Therefore, as a method for three-dimensionally visualizing temperature rise, a method is proposed in which a phantom with temperature-sensitive liquid crystal (cholesteric liquid crystal or the like) enclosed therein is created to visualize temperature rise due to a device by a slit light source. (see, e.g., Iwahashi et al., Adv Biomed Eng. 7: pp. 1-7, 2018).

SUMMARY

A main object of the method of visualizing temperature rise due to a device by a slit light source is, however, to evaluate temperature rise of a high-intensity focused ultrasound (HIFU) treatment device. In the case of evaluation of the renal denervation treatment device described before, when the light source is scanned, with a camera being fixed, the distance between the camera and an object (a surface irradiated by the slit light source) changes, and the camera is not focused. Therefore, there is a possibility that a clear image is not taken.

In order to solve the above problem, a system according to claim 1 is a system for quantitatively evaluating a treatment device capable of radiating ultrasound for heating human tissue, the system including:
  simulated tissue having a property that hue changes according to temperature in a particular temperature-sensitive area, the simulated tissue simulating temperature change of human tissue at time of the human tissue receiving the ultrasound from the treatment device;
  a light source radiating planar light to the simulated tissue;
  an image taking device taking cross-sectional color images of light irradiation surfaces of the simulated tissue;
  movement mechanisms causing the light source and the image taking device to relatively move in a photographing axis direction of the image taking device relative to the simulated tissue;
  a color-temperature conversion table for converting from hues of the images of the simulated tissue to temperatures; and
  movement mechanism control/information processing means for controlling the movement mechanisms so that the light source and the image taking device move in a state of keeping a distance between the light irradiation surface and the image taking device constant, and further acquiring temperature distributions of the simulated tissue from the hues at positions on the taken images of the simulated tissue, using the color-temperature conversion table.

If a system according to claim 2 is the system according to claim 1, wherein the movement mechanism control/information processing means acquires the temperature distributions in the photographing axis direction of the simulated tissue, from images taken under image taking conditions using the color-temperature conversion table and outputs three-dimensional temperature distribution from the temperature distributions of the simulated tissue, it is preferable because it is possible to three-dimensionally grasp the temperature distributions of the simulated tissue.

If a system according to claim 3 is the system according to claim 1 or 2, further including image holding means for holding the acquired temperature distributions of the simulated tissue as images, wherein the movement mechanism control/information processing means outputs temporal temperature-distribution change of the simulated tissue based on the held temperature distribution images, it is preferable in comparison with the case without the present configuration because it is possible to evaluate temperature-distribution change of the simulated tissue on a time axis.

If a system according to claim 4 is the system according to any one of claims 1 to 3, further including a thermocouple arranged in the simulated tissue, wherein the movement mechanism control/information processing means creates the color-temperature conversion table based on measured temperatures by the thermocouple and the hues of the images of the simulated tissue, it is preferable in comparison with the case without the present configuration because it is possible to evaluate the temperature distributions of the simulated tissue more accurately.

If a system according to claim 5 is the system according to any one of claims 1 to 3, further including a water tank capable of adjusting water temperature and accommodating the simulated tissue, wherein the movement mechanism control/information processing means creates the color-temperature conversion table based on water temperatures of the water tank and hues of images of the simulated tissue accommodated in water in the water tank, it is preferable in comparison with the case without the present configuration because it is possible to grasp the temperature distributions of the simulated tissue more accurately without using the calibration simulated tissue.

If a system according to claim 6 is the system according to any one of claims 1 to 5, wherein the light source surrounds the simulated tissue from 360-degree directions, it is preferable because it is possible to take the images of the simulated tissue, with effects of shadows of the treatment device arranged in an insertion hole of the simulated tissue being excluded.

If a system according to claim 7 is the system according to any one of claims 1 to 5, wherein the light source is arranged at each of symmetrical positions sandwiching the simulated tissue, it is preferable because it is possible to take the images of the simulated tissue, with the effects of the shadows of the treatment device arranged in the insertion hole of the simulated tissue being reduced.

In order to solve the above problem, a program according to claim 8 is a program used in a system for evaluating a treatment device capable of radiating ultrasound for heating human tissue, the system including:

simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;

two light sources radiating planar light to the simulated tissue, the two light sources being arranged at symmetrical positions sandwiching the simulated tissue;

an image taking device taking cross-sectional color images of light irradiation surfaces of the simulated tissue;

movement mechanisms causing the light source and the image taking device to relatively move in a photographing axis direction of the image taking device relative to the simulated tissue;

a color-temperature conversion table for converting from hues of the images of the simulated tissue to temperatures;

movement mechanism control-information processing means for controlling the movement mechanisms so that the light source and the image taking device move in a state of keeping a distance between the light irradiation surface and the image taking device constant, and further acquiring temperature distributions of the simulated tissue from the hues at positions on the taken images of the simulated tissue, using the color-temperature conversion table; and a first thermocouple arranged in a first area (Cal_1) near the insertion hole in the simulated tissue, the first area (Cal_1) not overlapping with the insertion hole of the simulated tissue when seen from any one of the light sources, and a second thermocouple arranged in a second area (Cal_2) overlapping with the insertion hole of the simulated tissue; and the treatment device being arranged in the insertion hole of the simulated tissue; wherein the program causes the movement mechanism control/information processing means to execute:

a heating process of causing the treatment device to radiate the ultrasound to heat the simulated tissue;

a monitoring process of monitoring color change of the heated simulated tissue near the first and second thermocouples through the image taking device;

a stop process of, when the color change of the simulated tissue near the first and second thermocouples is observed, causing the radiation of the ultrasound by the treatment device to stop;

a temperature measurement process of causing each of the first and second thermocouples to measure temperature of the simulated tissue;

a first image taking process of causing the image taking device to take an image of the simulated tissue;

an image division process of dividing the taken image into the first area (Cal_1) and the second area (Cal_2);

a first table calibration process of calibrating table values of the color-temperature conversion table corresponding to the first area (Cal_1) based on the measured temperature and a hue of a position closest to a position of the first thermocouple in the first area (Cal_1); and a second table calibration process of calibrating table values of the color-temperature conversion table corresponding to the second area (Cal_2), based on the measured temperature and a hue of a position closest to a position of the second thermocouple in the second area (Cal_2).

If a program according to claim 9 is the program according to claim 8, further causing the movement mechanism control/information processing means to, until the simulated tissue reaches a lower-limit temperature of the temperature-sensitive area, repeatedly execute at predetermined time intervals: a second image taking process of causing the image taking device to take an image of the simulated tissue, the image division process of dividing the taken image into the first area (Cal_1) and the second area (Cal_2), and a temperature distribution acquisition process of acquiring temperature distribution from each of the first area (Cal_1) and the second area (Cal_2) of the simulated tissue, using the calibrated color-temperature conversion table, it is preferable in comparison the case without the present configuration because, by using the color-temperature conversion table calibrated for each area, the effects of the shadows of the treatment device arranged in the insertion hole of the simulated tissue are reduced.

If a program according to claim 10 is the program according to claim 9, wherein the system further includes image holding means for holding the acquired temperature distribution of the simulated tissue as an image, the temperature distribution acquisition process includes an image holding process of the image holding means holding the acquired temperature distribution, and the program causes the movement mechanism control/information processing means to execute an output process of outputting temporal temperature-distribution change of the simulated tissue, in response to a request by a system user, it is preferable because it is possible to evaluate the temperature distribution change for the entire temperature-sensitive area of the simulated tissue on the time axis.

In order to solve the above problem, a program according to claim 11 is a program used in a system for evaluating a treatment device capable of radiating ultrasound for cauterizing human tissue, the system including:

- simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;
- two light sources radiating planar light to the simulated tissue, the two light sources being arranged at symmetrical positions sandwiching the simulated tissue;
- an image taking device taking cross-sectional color images of light irradiation surfaces of the simulated tissue;
- movement mechanisms causing the light sources and the image taking device to relatively move in a photographing axis direction of the image taking device relative to the simulated tissue;
- a color-temperature conversion table for converting from hues of the images of the simulated tissue to temperatures;
- movement mechanism control/information processing means for controlling the movement mechanisms so that the light sources and the image taking device move in a state of keeping a distance between the light irradiation surface and the image taking device constant, and further acquiring temperature distributions of the simulated tissue from the hues at positions on the taken images of the simulated tissue, using the color-temperature conversion table; and
- a water tank capable of adjusting water temperature and accommodating the simulated tissue, wherein the program causes the movement mechanism control/information processing means to execute:

- a temperature control process of controlling water in the water tank to be at a predetermined temperature;
- an image taking process of causing the image taking device to take an image of the simulated tissue accommodated in the water in the water tank;
- an image division process of dividing the taken image into a first area (Cal_1) not overlapping with the insertion hole of the simulated tissue when seen from the light sources and a second area (Cal_2) overlapping with the insertion hole; and
- a table calibration process of calibrating the color-temperature conversion table for each of the first area (Cal_1) and the second area (Cal_2) based on the water temperature in the water tank and the hues of the image of the simulated tissue; and
- the program further causes the movement mechanism control/information processing means to repeatedly execute the temperature control process, the image taking process, the image division process, and the table calibration process for the entire temperature-sensitive area from a lower-limit temperature to an upper-limit temperature of the temperature-sensitive area of the simulated tissue.

If a program according to claim 12 is the program according to claim 11, wherein, in the system, the treatment system is arranged in the insertion hole of the simulated tissue, the program causes the movement mechanism control/information processing means to execute: a heating process of causing the treatment device to radiate the ultrasound to heat the simulated tissue, an image taking process of causing the image taking device to take an image of the simulated tissue at predetermined time intervals, the image division process of dividing the taken image into the first area (Cal_1) and the second area (Cal_2), and a temperature distribution acquisition process of acquiring temperature distribution from each of the first area (Cal_1) and the second area (Cal_2) of the simulated tissue, using the calibrated color-temperature conversion table, and the program causes the movement mechanism control/information processing means to repeatedly execute the heating process, the image taking process, the image division process, and the temperature distribution acquisition process for the entire temperature-sensitive area from the lower-limit temperature to the upper-limit temperature of the temperature-sensitive area of the simulated tissue, it is preferable because it is possible to acquire the temperature distribution change for the entire temperature-sensitive area of the simulated tissue on the time axis.

If a program according to claim 13 is the program according to claim 12, wherein the system further includes image holding means for holding the acquired temperature distributions of the simulated tissue as images, the temperature distribution acquisition process includes an image holding process of the image holding means holding the acquired temperature distribution, and the program causes the movement mechanism control/information processing means to execute an output process of outputting temporal temperature-distribution change of the simulated tissue, in response to a request by a system user, it is preferable because it is possible to evaluate the temperature distribution change for the entire temperature-sensitive area of the simulated tissue on the time axis.

In order to solve the above problem, a method for calibration according to claim 14 is a method for calibrating measurement of a system for evaluating a treatment device capable of radiating ultrasound for cauterizing human tissue, the system including:

- simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;
- a light source radiating planar light to the simulated tissue;
- an image taking device taking cross-sectional color images of light irradiation surfaces of the simulated tissue;
- movement mechanisms causing the light source and the image taking device to relatively move in a photographing axis direction of the image taking device relative to the simulated tissue;
- a color-temperature conversion table for converting from hues of the images of the simulated tissue to temperatures;
- movement mechanism control/information processing means for controlling the movement mechanisms so that the light source and the image taking device move in a state of keeping a distance between the light irradiation surface and the image taking device constant, and further acquiring temperature distributions of the simulated tissue from taken images of the hues at positions of the simulated tissue using the color-temperature conversion table; and
a thermocouple arranged in the simulated tissue; and
the treatment device being arranged in the insertion hole of the simulated tissue; wherein
the method includes:
a process of the treatment device radiating the ultrasound to heat the whole simulated tissue;
a process of monitoring color change of the heated simulated tissue near the thermocouple;
a process of, when the color change of the simulated tissue near the thermocouple is observed, stopping the radiation of the ultrasound by the treatment device;
a process of the thermocouple measuring temperatures of the simulated tissue;
a process of the image taking device taking the images of the simulated tissue; and
a process of calibrating the color-temperature conversion table based on the measured temperatures and hues near the thermocouple on the taken images.

In order to solve the above problem, a method for calibration according to claim 15 is a method for calibrating measurement of a system for evaluating a treatment device capable of radiating ultrasound for cauterizing human tissue, the system including:
simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;
a light source radiating planar light to the simulated tissue;
an image taking device taking cross-sectional color images of light irradiation surfaces of the simulated tissue;
movement mechanisms causing the light source and the image taking device to relatively move in a photographing axis direction of the image taking device relative to the simulated tissue;
a color-temperature conversion table for converting from hues of the images of the simulated tissue to temperatures;
movement mechanism control/information processing means for controlling the movement mechanisms so that the light source and the image taking device move in a state of keeping a distance between the light irradiation surface and the image taking device constant, and further acquiring temperature distributions of the simulated tissue from the hues at positions on the taken images of the simulated tissue, using the color-temperature conversion table; and
a water tank capable of adjusting water temperature and accommodating the simulated tissue; wherein
the method includes:
a process of taking an image of the simulated tissue accommodated in water in the water tank controlled to be at a predetermined temperature; and
a process of changing the water temperature in the water tank for the entire temperature-sensitive area from a lower-limit temperature to an upper-limit temperature of the simulated tissue to repeat the process of taking an image, and calibrating the color-temperature conversion table for the entire temperature-sensitive area based on water temperatures in the water tank and hues of taken images of the simulated tissue.

According to the present invention, it is possible to, in a system for evaluating a treatment device capable of radiating ultrasound to cauterize human tissue, prevent occurrence of defocus to acquire a clear image.

BRIEF DESCRIPTION OF DRAWINGS

FIG. 7(a) shows a relationship between RGB values (vertical axis) and temperature (horizontal axis) acquired by the image taking device and a thermocouple at the time of using a temperature-sensitive phantom that becomes colored within a range of 60° C. to 70° C., FIG. 7(b) is a diagram of, by performing principal component analysis for the acquired RGB values, the RGB values being projected onto first principal components (horizontal axis) and second principal components (vertical axis), and FIG. 7(c) shows a table (a color-temperature conversion table) obtained by acquiring, based on a centroid X of the pieces of projected data, data of a phase angle/temperature of each of the pieces of projected data and associating the phase angle and the temperature one to one.

FIG. 9 shows a time profile of temperature distributions obtained by extracting only an area with a temperature rise of 63° C. or more in obtained temperature rise distribution of the temperature-sensitive phantom, and cutting the area at a cross section of X=0 (an example of a display method).

FIG. 11 is a diagram illustrating states at the time of irradiating the calibration temperature-sensitive phantom with light using a light source/light sources in which FIG. 11(a) shows a state at the time of radiating light from one direction (to the calibration temperature-sensitive phantom from a right direction of FIG. 11(a)), and FIG. 11(b) shows a state at the time of radiating light from both sides of the calibration temperature-sensitive phantom, with the calibration temperature-sensitive phantom being sandwiched.

FIG. 13 is a schematic diagram of the color-temperature conversion table for each of the first and second areas in FIG. 12.

DETAILED DESCRIPTION

The present invention will be described below using embodiments applied to a renal denervation device. The present invention, however, is not limited thereto and is applicable to performance evaluation of treatment devices for other diseases and treatment devices using an RF catheter. For example, in hypertension treatment, renal denervation treatment lowers blood pressure by cauterizing sympathetic nerves around renal vessels through a catheter. For example, RF (electrode) cauterization and ultrasonic cauterization are included within the application range.

First Embodiment

Figure 1:
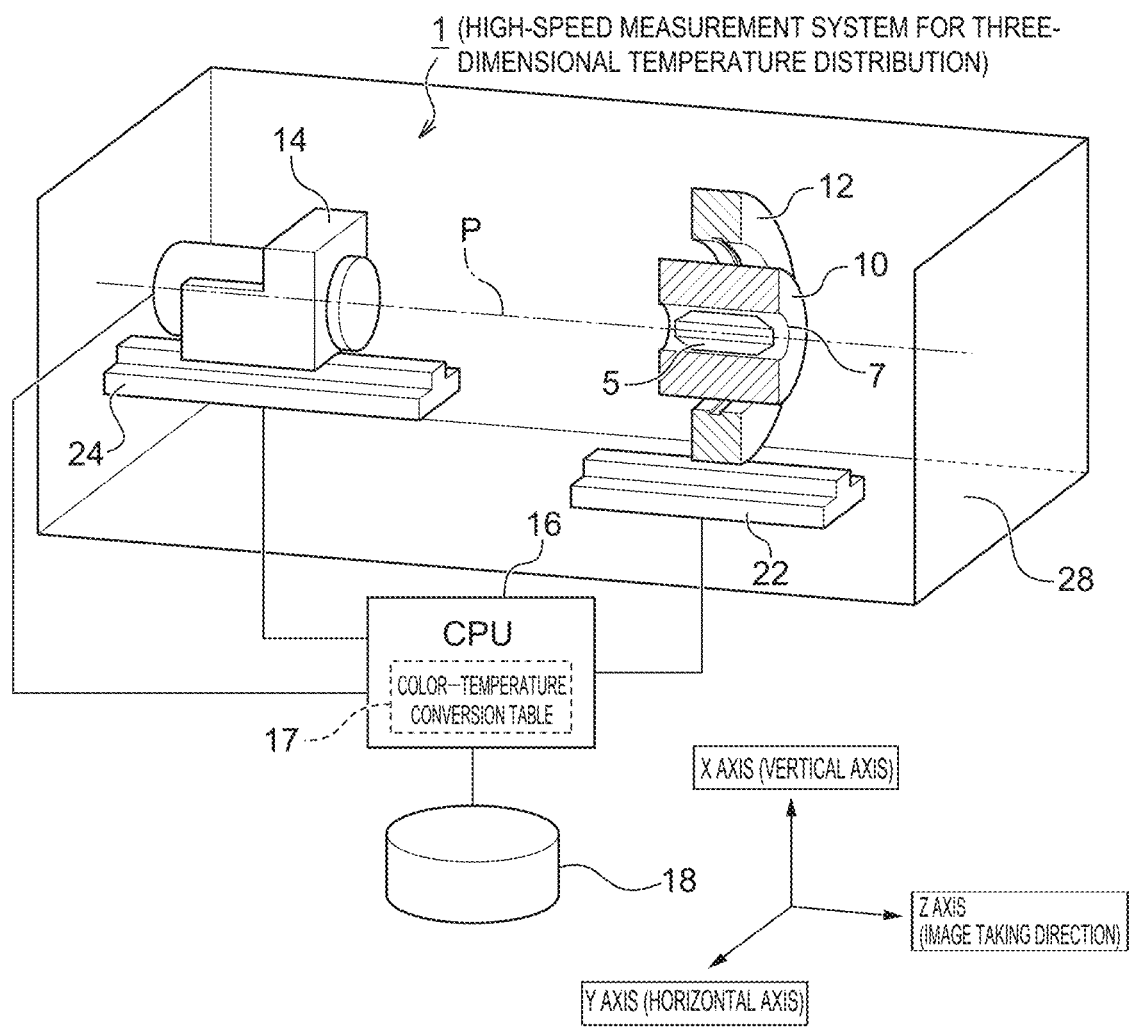
FIG. 1 is a schematic diagram showing a configuration of a three-dimensional temperature distribution high-speed measurement system according to a first embodiment.
Figure 2:
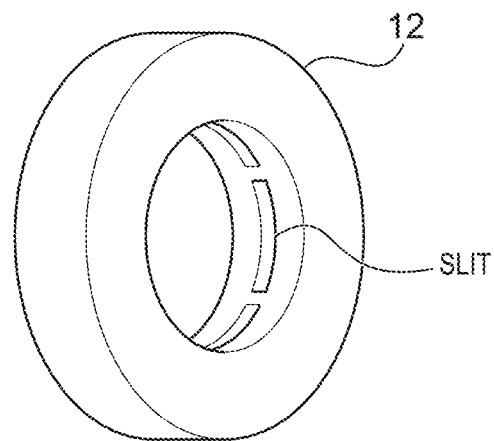
FIG. 2 is an external view of a light source used in the three-dimensional temperature distribution high-speed measurement system shown in FIG. 1.

FIG. 1 is a schematic diagram showing a configuration of a three-dimensional temperature distribution high-speed measurement system 1 according to a first embodiment, and FIG. 2 is an external view of a light source used in the three-dimensional temperature distribution high-speed measurement system 1 shown in FIG. 1. Here, as for the expression of "high-speed", the expression of "high-speed" is used in comparison in the case of measuring a HIFU sound field using a hydrophone (an ultrasonic sensor) or the like described before. In the sound field measurement using a normal hydrophone, since the hydrophone is caused to mechanically perform scanning, one to two hours and three to four hours are required in two-dimensional sound field measurement and in three-dimensional measurement, respectively, though it depends on the measurement pitch and the measurement range. In comparison, in the present system, since it is possible to instantly acquire a two-dimensional optical image and perform three-dimensional measurement only by single-axis mechanical scanning, measurement can be performed at a high speed in about 1/200th of the time (two-dimensional: several seconds to several tens of seconds; three-dimensional: several tens of seconds to several minutes) in comparison with the sound field measurement by a hydrophone.

The three-dimensional temperature distribution high-speed measurement system 1 is configured, including a temperature-sensitive phantom 10 configured with semi-transparent material having a property that its hue changes according to temperature; a donut-shaped light source 12 arranged surrounding the temperature-sensitive phantom 10 placed at a position of the hole of the donut, the donut-shaped light source 12 radiating planar light to the temperature-sensitive phantom 10 from the whole circumference; an image taking device 14 configured, for example, with a CCD camera, the image taking device 14 taking images of the whole temperature-sensitive phantom 10 from a direction of a photographing axis P that is vertical relative to the plane of the light radiated from the light source 12; a movement mechanism control/information processing unit 16 as an example of movement mechanism control/information processing means, which is configured, for example, with an information processing device (CPU) and includes a color-temperature conversion table 17 for converting from hues of an image of the temperature-sensitive phantom 10 to corresponding temperatures, the movement mechanism control/information processing unit 16 acquiring temperature distribution of the temperature-sensitive phantom 10 from hues at positions on a taken image of the temperature-sensitive phantom 10 and controlling a light source movement mechanism 22 and an image taking device movement mechanism 24 to be described later; and an image holding unit 18 as an example of image holding means, which is configured with storage means, for example, a memory or an HD, the image holding unit 18 holding the temperature distribution acquired from the taken image of the temperature-sensitive phantom 10 as an image. When the light source 12 radiates planar light to the temperature-sensitive phantom 10, the image taking device 14 takes a cross-sectional color image of the temperature-sensitive phantom 10 on a light irradiation surface.

The temperature-sensitive phantom 10 is configured having an insertion hole 7, which extends in the direction of the photographing axis P of the image taking device 14 and simulates a blood vessel diameter, to accept a treatment device 5 (to be described later). The temperature-sensitive phantom 10 functions as simulated tissue that simulates temperature change of human tissue when receiving ultrasound from the treatment device 5 arranged in the insertion hole 7 and increasing in temperature. The light source 12 has LEDs arranged in a donut shape and is configured having slits that emit light to the temperature-sensitive phantom 10 on the inner side of the donut hole (see FIG. 2). The image taking device 14 is arranged such that the photographing axis passes through the center (the insertion hole 7) of the temperature-sensitive phantom 10 to take images of the whole temperature-sensitive phantom 10. The image holding unit 18 holds an acquired temperature distribution image of the temperature-sensitive phantom 10, and the movement mechanism control/information processing unit 16 outputs temporal temperature-distribution change of the temperature-sensitive phantom 10. Here, the treatment device 5 is configured, including a single-plate cylindrical ultrasonic transducer capable of radiating ultrasound to cauterize human tissue or an ultrasonic array transducer configured with a plurality of micro ultrasonic transducers. As an example of human tissue, sympathetic nerves around a renal artery or blood vessel walls of the renal artery are conceivable.

Further, the three-dimensional temperature distribution high-speed measurement system 1 includes, as examples of movement mechanisms to cause the light source 12 and the image taking device 14 to relatively move in the direction of the photographing axis P relative to the temperature-sensitive phantom 10, the light source movement mechanism 22, which is configured, for example, with a motor, a linear guide, and the like and causes the light source 12 to move parallel to the direction of the photographing axis P of the image taking device 14, and the image taking device movement mechanism 24, which is similarly configured with a motor, a linear guide, and the like and causes the image taking device 14 to move parallel to the direction of the photographing axis P. Before measurement, a measurement range and a distance between measurement surfaces (a pitch or the like) are set in advance by the movement mechanism control/information processing unit 16. Here, the light source movement mechanism 22 and the image taking device movement mechanism 24 are configured to be controlled to operate together in the direction of the photographing axis P by the movement mechanism control/information processing unit 16 to keep a distance between the light irradiation surface and the image taking device 14 constant. Thereby, the image taking device 14 is in a state of being focused on the light irradiation surface (a focus surface) during movement, and it becomes possible to cause the light source 12 and the image taking device 14 to move together so that the light irradiation surface moves in the direction of the photographing axis P from the farthest position to the closest position of the temperature-sensitive phantom 10 when seen from the image taking device 14, and sequentially take cross-sectional images of the whole temperature-sensitive phantom 10. The taken images of the whole temperature-sensitive phantom 10 are held by the image holding unit 18. The light source movement mechanism 22 can finely adjust the position of the image taking device 14 independently from the operation of the image taking device movement mechanism 24 and can cause the image taking device 14 to be focused on the light irradiation surface. The three-dimensional temperature distribution high-speed measurement system 1 is arranged in a blackout box 28 to exclude effects of external light.

Here, a specific procedure measurement preparation process/evaluation process by the three-dimensional temperature distribution high-speed measurement system 1 will be shown. As a preparation process before starting evaluation, calibration work for associating changes in hue (RGB values acquired by the image taking device 14) due to temperature rise of the temperature-sensitive phantom 10 with actual temperatures is performed. Here, a calibration method will be described, and then an evaluation method will be described.

Calibration Method

Figure 3:
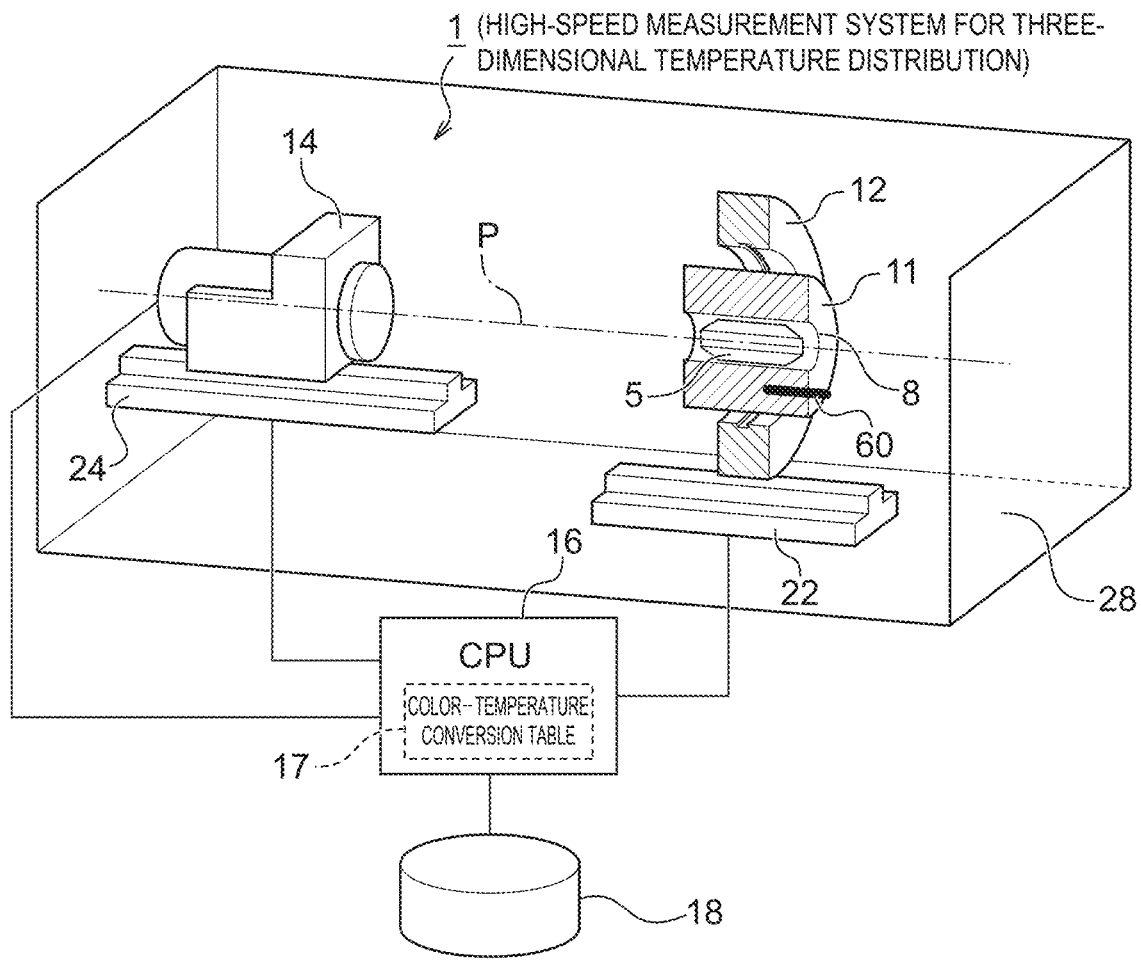
FIG. 3 is a schematic diagram showing a configuration of the three-dimensional temperature distribution high-speed measurement system according to the first embodiment at the time of calibration.

FIG. 3 is a schematic diagram showing a configuration of the three-dimensional temperature distribution high-speed measurement system 1 at the time of calibration. As shown in FIG. 3, a calibration temperature-sensitive phantom 11 is set in the three-dimensional temperature distribution high-speed measurement system 1. Here, it is necessary that the calibration temperature-sensitive phantom 11 is formed with a temperature-sensitive phantom of the same lot as the evaluation temperature-sensitive phantom 10, and the shape, size, and the like are also the same. This is because, if the temperature-sensitive phantoms for calibration and evaluation are different in the concentration of temperature-sensitive material, the phantom shape, and the like, there is a possibility that the color-temperature conversion relationship is different at the time of calibration and at the time of evaluation.

Figure 4:
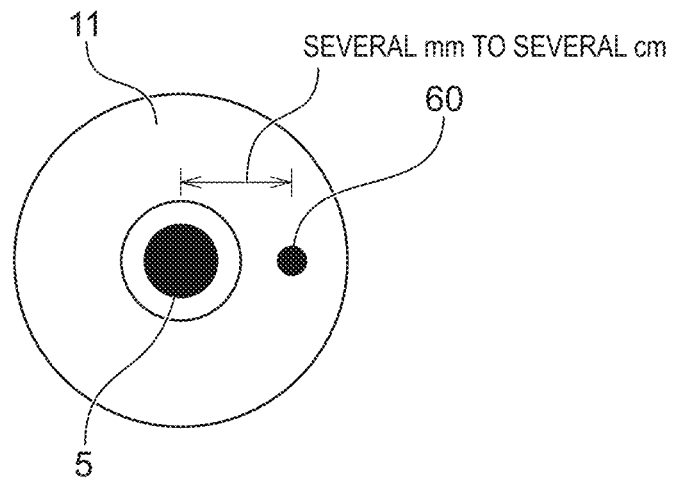
FIG. 4 is a front view at the time of taking an image of a temperature-sensitive phantom at the time of calibration according to the first embodiment from an image taking device.

In order to acquire a relationship between temperature and hue, a thermocouple 60 is inserted into the calibration temperature-sensitive phantom 11. FIG. 4 is a front view of an image of the calibration temperature-sensitive phantom 11 which is taken by the image taking device 14. As shown in FIG. 4, the thermocouple 60 is inserted about several millimeters to several centimeters away from the treatment device 5. It is not possible to generally define the insertion position because an optimal position depends on the sizes of the treatment device 5 and a temperature rise area. The insert position is only required to be in an area where the relationship between hue and temperature of the temperature-sensitive material can be acquired.

Initial Setting (Focusing)

Figure 5:
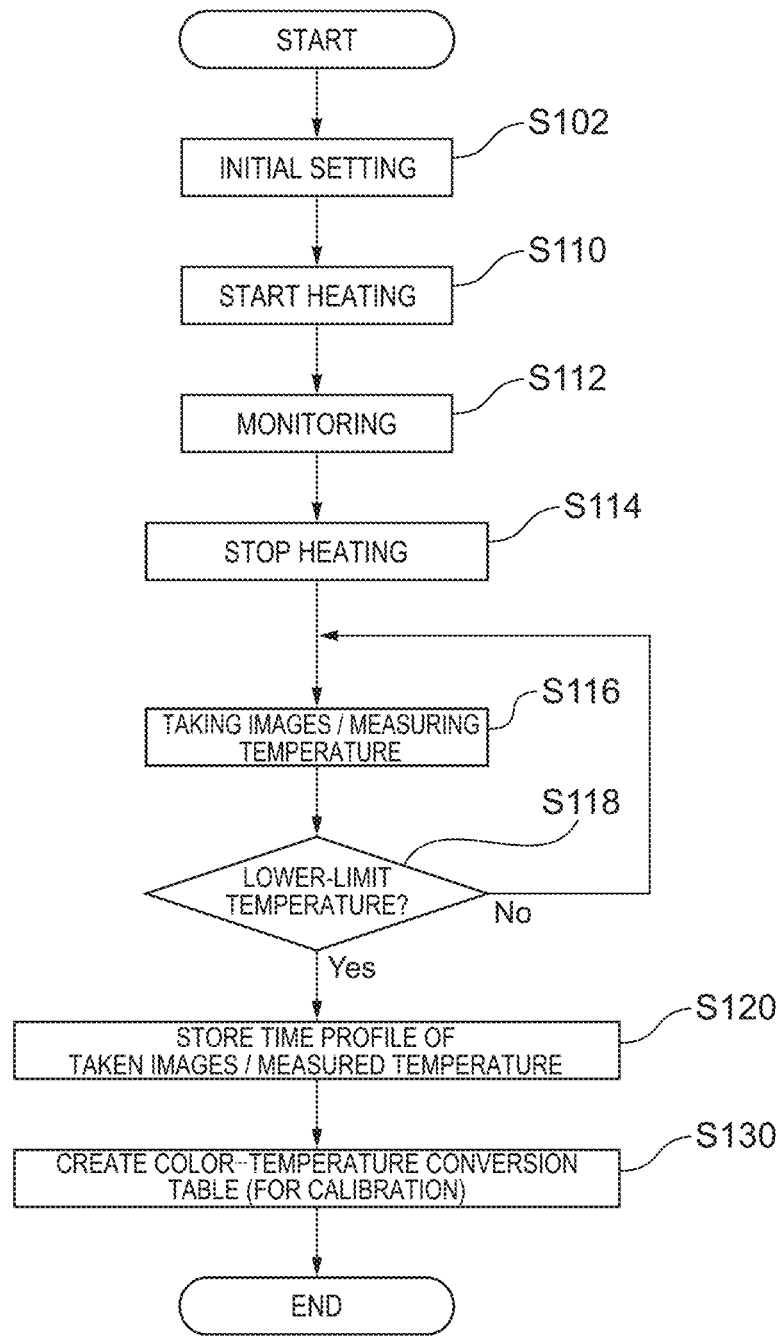
FIG. 5 is a flowchart of a calibration method executed in the three-dimensional temperature distribution high-speed measurement system according to the first embodiment.

A calibration method executed in a state of the treatment device 5 being arranged in an insertion hole 8 of the calibration temperature-sensitive phantom 11 in the three-dimensional temperature distribution high-speed measurement system 1 will be described. FIG. 5 is a flowchart of the calibration method executed in the three-dimensional temperature distribution high-speed measurement system 1. First, the light source 12 radiates planar light to the calibration temperature-sensitive phantom 11: the image taking device 14 photographs the calibration temperature-sensitive phantom 11: and it is confirmed whether the image taking device 14 is focused on the position of the light irradiation surface. If the image taking device 14 is not focused, the image taking device movement mechanism 24 operates and finely adjusts the position of the image taking device 14 to correct defocus. When the image taking device 14 is focused, the light source movement mechanism 22 and the image taking device movement mechanism 24 work together to cause the position of the light irradiation surface and the image taking device 14 to move to an initial position (in the present embodiment, near the center of the calibration temperature-sensitive phantom 11) in a state of keeping the distance between the light irradiation surface and the image taking device 14 constant, and the initial setting process (S102) is completed.

Acquisition of Hue-Temperature Data for Calibration

When the initial setting is completed, the movement mechanism control/information processing unit 16 causes the treatment device 5 to start and causes ultrasound radiation to start. Receiving the ultrasound radiation from the treatment device 5, the calibration temperature-sensitive phantom 11 vibrates, and the temperature of the whole calibration temperature-sensitive phantom 11 rises (a heating process: S110). At this time, the movement mechanism control/information processing unit 16 monitors color change of the calibration temperature-sensitive phantom 11 through the image taking device 14 (a monitoring process: S112). When the temperature rise area expands to the area that includes the thermocouple 60 while performing monitoring, output of the treatment device 5 is stopped (a heating stop process: S114). After heating is stopped, image taking/temperature measurement is started in order to acquire a relationship between the hue of the calibration temperature-sensitive phantom 11 and actual temperature (a temperature/image measurement process: S116). The image taking/temperature measurement is repeated until the thermocouple reaches the lower-limit value of the phantom coloration temperature (S118).

Figure 6:
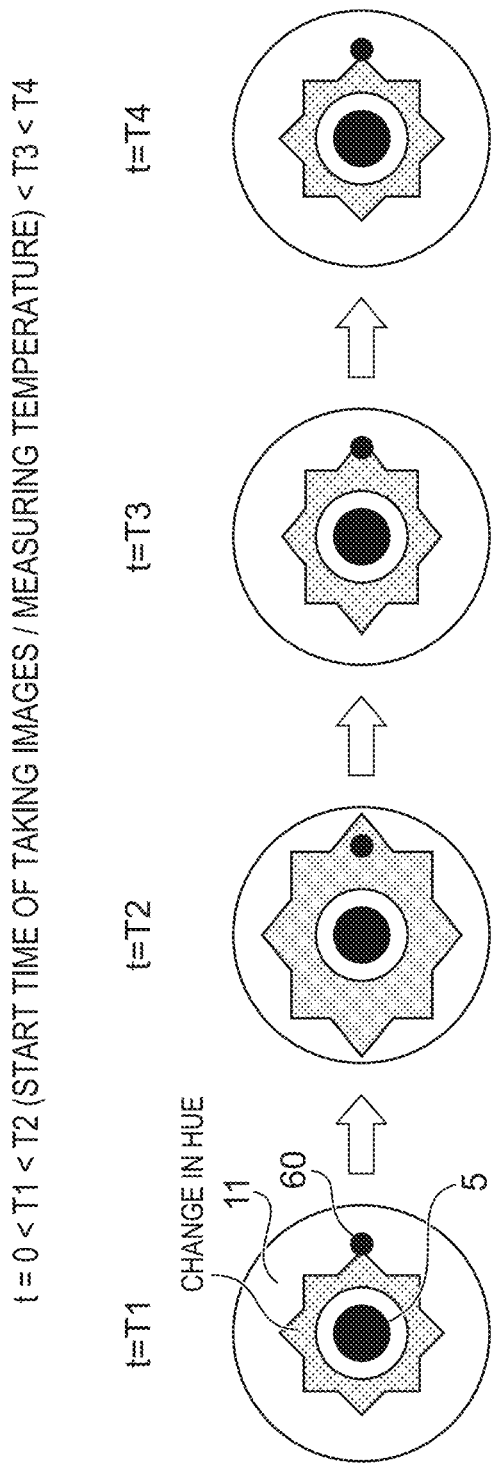
FIG. 6 shows a time profile of front views at the time of taking images of the calibration temperature-sensitive phantom 11 from the image taking device 14 in calibration executed in the three-dimensional temperature distribution high-speed measurement system according to the first embodiment.

An overview of the process from S110 to S118 of the above flowchart is shown by FIG. 6. FIG. 6 shows a time profile of front views at the time of taking images of the calibration temperature-sensitive phantom 11 from the image taking device 14. When time is 0, output of the treatment device 5 is turned on to start heating of the calibration temperature-sensitive phantom 11 (S110). The calibration temperature-sensitive phantom 11 gradually begins to be colored from an area near the treatment device 5. When the colored area expands to the thermocouple 60 area (t=T2), heating is stopped (S114), and image taking/temperature measurement is started (S116: a first image taking process). After that, the image taking/temperature measurement is repeated until the thermocouple reaches the lower-limit value of the phantom coloration temperature as described before (S118).

By separating temperature rise of the calibration temperature-sensitive phantom 11 due to ultrasound radiation from image taking of the calibration temperature-sensitive phantom 11 in a state of the ultrasound radiation being stopped as described above, it is possible to acquire the color-temperature conversion table 17 in a state in which effects of the temperature of a part near the thermocouple 60 becoming locally higher than other parts due to vibration of the thermocouple 60 caused by ultrasound radiation are excluded.

Calibration Using Obtained Data

Until the lower-limit value of the phantom coloration temperature is reached, hues (RGB values) and temperatures at the RGB values are measured, and a time profile thereof is stored (S120). Using the RGB values and values of the temperatures at the RGB values, creation of the color-temperature conversion table is performed (a calibration process: S130). Various methods can be proposed or conceived as methods for associating the hues and pieces of temperature information. Here, the method by principal component analysis of RGB values shown in Patent Literature I will be described. As for the calibration process, however, any means is possible without being limited to the above method if the means is a method that can associate a set of RGB values and a temperature one to one and can estimate temperatures from actual phantom hues.

FIG. 7(a) shows a relationship between RGB values (vertical axis) and temperature (horizontal axis) acquired with the image taking device 14 and the thermocouple 60 at the time of using the calibration temperature-sensitive phantom 11 that is colored within a range of 60° C. to 70° C. Here, by performing principal component analysis for the RGB values, the RGB values are projected to first primary components (horizontal axis) and second primary components (vertical axis) (FIG. 7(b)). Based on a centroid X of the pieces of projected data, phase angle/temperature data of each piece of projection data is acquired, and such a table that a phase angle and a temperature correspond to each other one to one is created (FIG. 7(c)). By doing so, actual coloration temperatures (RGB values) and temperatures are associated, and it is possible to estimate actual temperatures from hues of the calibration temperature-sensitive phantom 11 in actual estimation.

Evaluation Method

Figure 8:
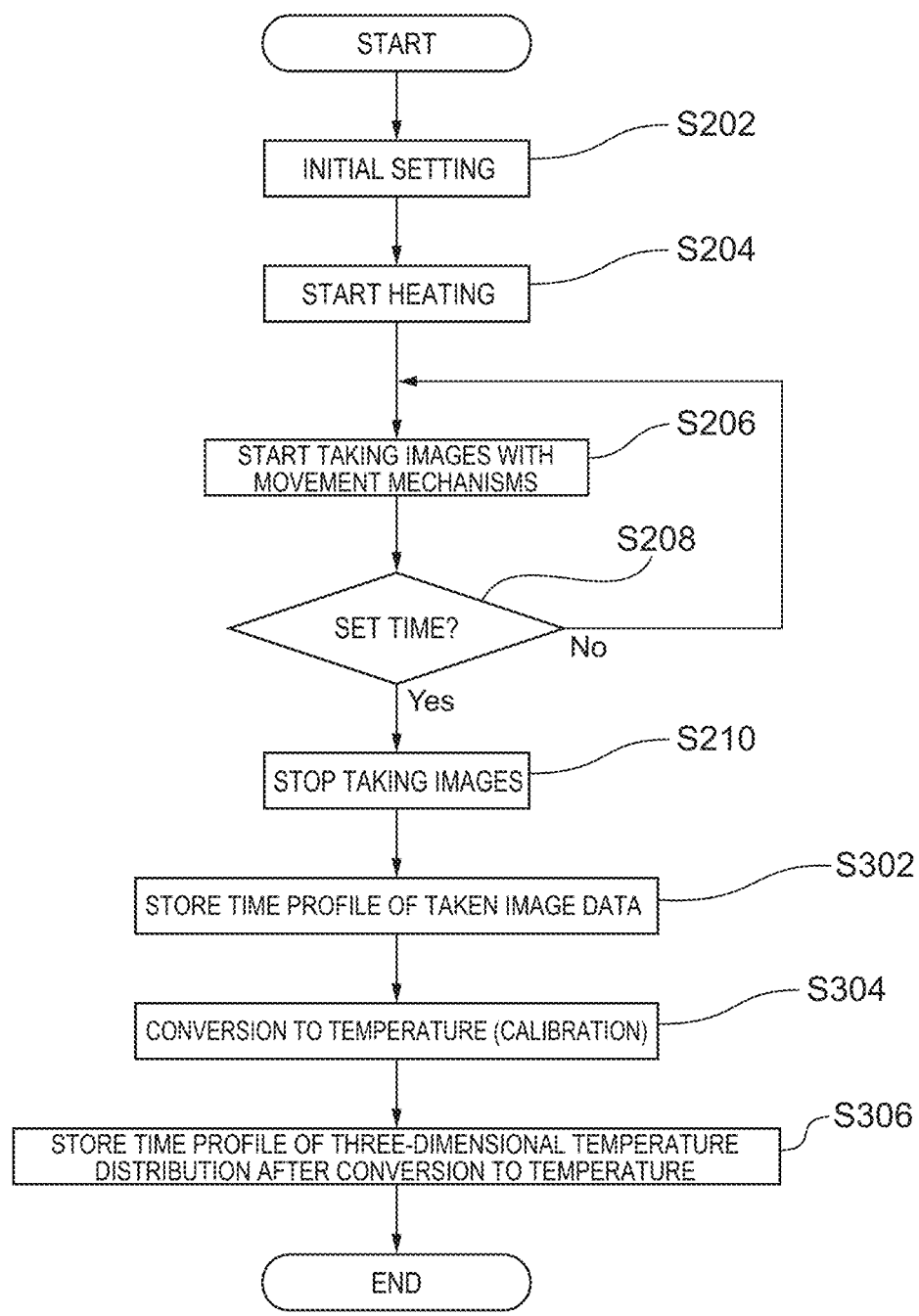
FIG. 8 is a flowchart of an evaluation method executed in the three-dimensional temperature distribution high-speed measurement system according to the first embodiment.

After the above calibration process ends, and the color-temperature conversion table 17 is stored into the movement mechanism control/information processing unit 16, actual temperature distribution measurement by the treatment device 5 is started by the system of FIG. 1. FIG. 8 shows a flowchart of evaluation. At initial setting S202, in addition to the focusing in the above calibration process, a range of three-dimensional distribution that a user wants to acquire, a distance (a pitch) between measurement surfaces, set image-taking time, and the like are set. After the initial setting is completed, heating is started (S204). The light source movement mechanism 22 and the image taking device movement mechanism 24 work together to move the light irradiation surface in the direction of the photographing axis P of the image taking device 14, and cross-sectional images of the whole evaluation temperature-sensitive phantom 10 in the direction of the photographing axis P are taken from the farthest position to the closest position of the evaluation temperature-sensitive phantom 10 when seen from the image taking device 14 (S206: a second image-taking process). Until the set image taking time is reached (S208: No), the image taking is repeated. When the set image taking time is reached (S208: Yes), the image taking is stopped (S210). After taking the image, a time profile of the taken image data is temporarily stored in the image holding unit 18 (S302); the movement mechanism control/information processing unit 16 performs temperature conversion using the color-temperature conversion table 17 stored in advance (S304): and a time profile of three-dimensional temperature distribution images into the image holding unit 18 (S306).

Temperature distribution of the evaluation temperature-sensitive phantom 10 is outputted to display means (not shown) in response to a request by the user (input means is not shown). Since profile images of three-dimensional temperature distributions at set times during evaluation are held in the image holding unit 18, it is also possible to display temporal temperature-distribution change in response a request by the user.

FIG. 9 shows an example of a time profile of diagrams of temperature distributions visualized and three-dimensionally displayed. FIG. 9 shows a time profile of temperature distributions obtained by extracting only an area of the evaluation temperature-sensitive phantom 10 with a temperature rise of 63° C. or more and cutting the area at a cross section of X=0. Thus, after the three-dimensional temperature distribution is acquired, it becomes possible to freely and quantitatively observe a surface, an angle, a time profile, and the like of temperature distribution that the user wants to observe. By doing so, it becomes possible to quantitatively confirm a states of a four-dimensional temperature rise area including an actual three-dimensional in vivo areas and a time dimension, and, therefore, it can be expected to be useful for safety check of a treatment device, formulation of a treatment plan, and the like.

Second Embodiment

Figure 10:
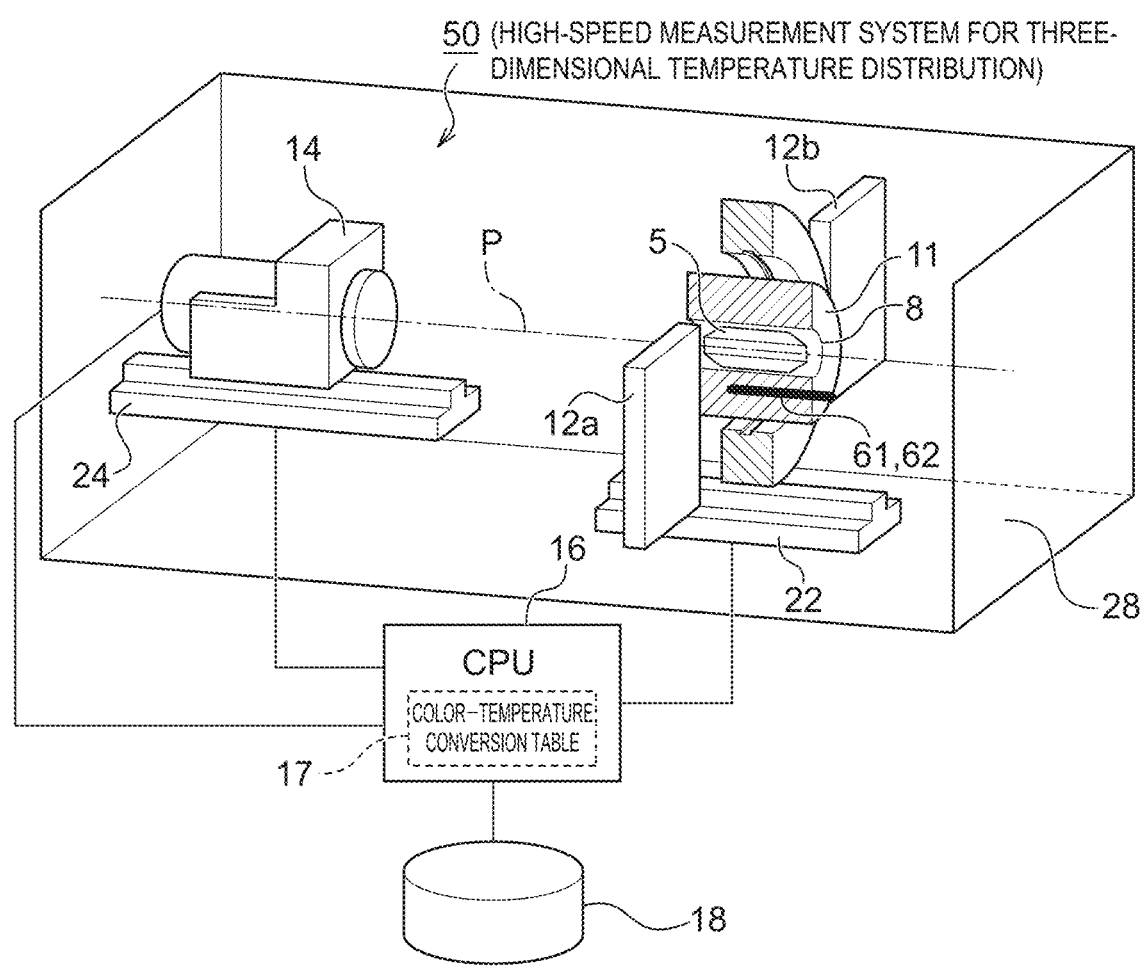
FIG. 10 is a schematic diagram showing a configuration of a three-dimensional temperature distribution high-speed measurement system according to a second embodiment at the time of calibration.

FIG. 10 is a schematic diagram showing a configuration of a three-dimensional temperature distribution high-speed measurement system 50 according to a second embodiment at the time of calibration. As for components that are the same as or similar to those of the three-dimensional temperature distribution high-speed measurement system 1 according to the first embodiment, the same or similar reference signs will be given, and description the components will be omitted. The three-dimensional temperature distribution high-speed measurement system 1 according to the first embodiment is configured such that light is radiated to each of the calibration temperature-sensitive phantom 11 and the evaluation temperature-sensitive phantom 10 from the whole circumference (see FIGS. 1 and 3). In comparison, the three-dimensional temperature distribution high-speed measurement system 50 according to the second embodiment described below is different in that light is radiated to the calibration temperature-sensitive phantom 11 and the evaluation temperature-sensitive phantom 10 from both left and right sides.

The three-dimensional temperature distribution high-speed measurement system 50 is configured, including light sources 12a and 12b that radiates planar light to the calibration temperature-sensitive phantom 11. The light sources 12a and 12b are arranged at symmetrical positions, sandwiching the calibration temperature-sensitive phantom 11 therebetween and radiate planar light to the whole calibration temperature-sensitive phantom 11 from both sides of the calibration temperature-sensitive phantom 11. Each of the light sources 12a and 12b is configured, for example, LEDs arranged in a line and slits arranged to emit light to the calibration temperature-sensitive phantom 11.

Figure 11:
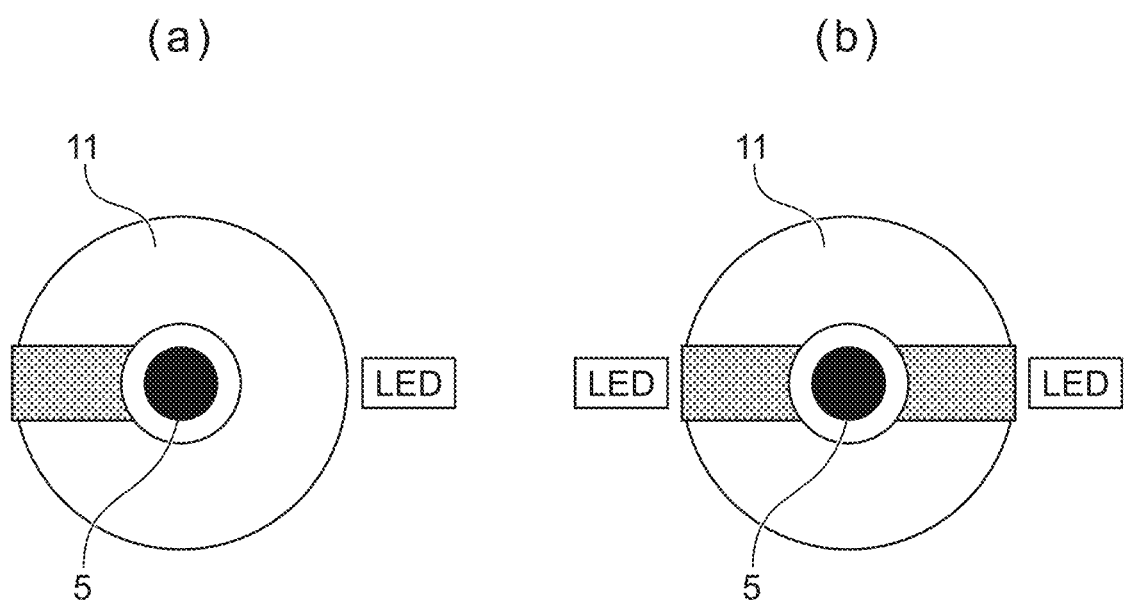

Here, description will be made on a state at the time of the light sources 12a and 12b radiating planar light to the calibration temperature-sensitive phantom 11, using drawings. FIG. 11 is a diagram illustrating states at the time of irradiating the calibration temperature-sensitive phantom 11 with light using the light sources 12a and 12b; FIG. 11(a) shows a state at the time of radiating light from one direction (to the calibration temperature-sensitive phantom 11 from a right direction of FIG. 11(a)); and FIG. 11(b) shows a state at the time of radiating light from both sides of the calibration temperature-sensitive phantom 11, with the calibration temperature-sensitive phantom 11 being sandwiched. As shown in FIG. 11(a), when light is radiated from the right direction of FIG. 11(a) (the light source 12a), a shadow is formed on the opposite side of the light source 12a across the treatment device 5, by the treatment device 5 arranged in the insertion hole 8. In comparison, when light is radiated, with the light sources 12a and 12b being arranged at symmetrical positions on both sides of the calibration temperature-sensitive phantom 11, effects of shadows of the treatment device 5 can be reduced as shown in FIG. 11(b). When temperature distribution of the calibration temperature-sensitive phantom 11 is carefully observed, however, it is seen that the effects of the shadows of the treatment device 5 are not completely excluded.

Figure 12:
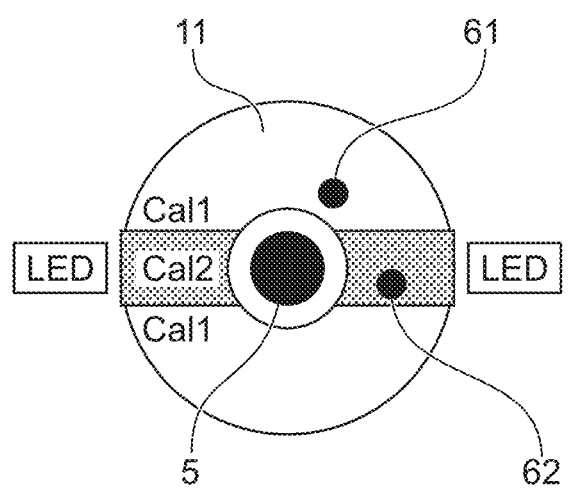
FIG. 12 is a diagram showing a state of an image acquired by being irradiated with light by the light sources being separated in a first area (Cal_1) that is not affected by shadows of a treatment device and a second area (Cal_2) that is affected by the shadows.

Description will be made on a calibration method for excluding the effects of the shadows when light is radiated from the light sources 12a and 12b arranged on both sides of the calibration temperature-sensitive phantom 11 will be described, using drawings. FIG. 12 is a diagram showing a state of an image acquired by being irradiated with light by the light sources 12a and 12b being separated in a first area (Cal_1) that is not affected by the shadows of the treatment device 5 and a second area (Cal_2) that is affected by the shadows. In the second area (Cal_2) affected by the shadows of the treatment device 5, that is, an opposite area (Cal_2_12a) relative to the light source 12a across the treatment device 5 and an opposite area (Cal_2_12b) relative to the light source 12b across the treatment device 5, the amount of light received from the light sources is smaller than that of the first area (Cal_1) that is not affected by the shadows of the treatment device 5. That is, the effects of the shadows of the treatment device 5 are not completely excluded.

Therefore, in order to exclude the effects of the shadows, two kinds of phantom hue-temperature relationships are acquired using a first thermocouple 61 inserted in the first area and a second thermocouple 62 inserted in the second area, and different color-temperature conversion is performed in each of the areas. A flowchart of a calibration method is almost similar to FIG. 5, the calibration method is different from the calibration method of the first embodiment in that temperature measurement is performed in each of the first and second areas (S116), and a color-temperature conversion table for each of the areas is created (S130). FIG. 13 shows an overview of the color-temperature conversion table for each of the first and second areas. Here, as calibration means for associating a hue and a temperature one to one, the method using main component analysis described before may be used, or other methods may be used.

Evaluation Method

A flowchart of the evaluation method in the second embodiment is also almost similar to that of the first embodiment (FIG. 8). The flowchart is different in that the user sets ranges of the first and second areas at the time of initial setting and that the stored color-temperature conversion table for each of the areas (FIG. 13) is used at the time of temperature conversion (S304). It is the same as the first embodiment that temperature distribution of the temperature-sensitive phantom 10 and temporal temperature-distribution change can be outputted in response to a request by the user (the input means is not shown).

Figure 14A:
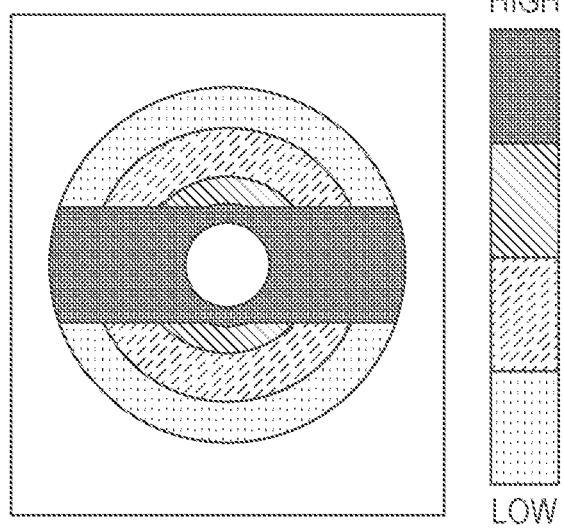
FIG. 14A shows temperature distribution of the whole sensitive-temperature phantom acquired using values that are obtained by calibrating values of the whole color-temperature conversion table based on temperatures of the temperature-sensitive phantom and hues of the first area (Cal_1).
Figure 14B:
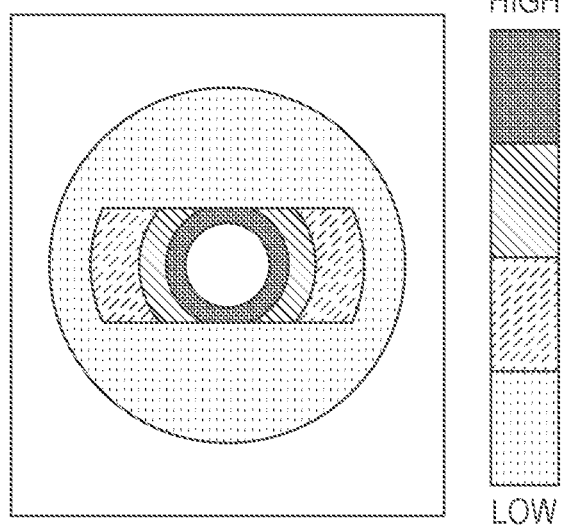
FIG. 14B shows temperature distribution of the whole sensitive-temperature phantom acquired using values that are obtained by calibrating values of the whole color-temperature conversion table based on temperatures of the temperature-sensitive phantom and hues of the second area (Cal_2).
Figure 14C:
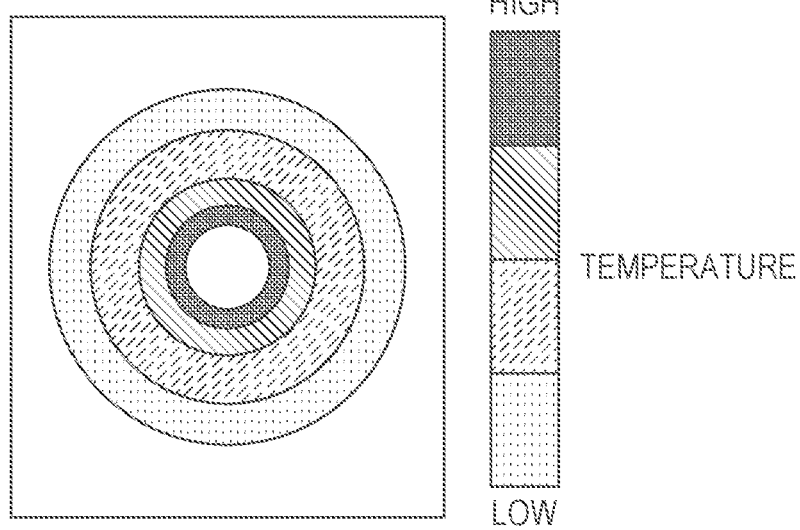
FIG. 14C shows a result of combining the temperature distribution of the first area (Cal_1) of the temperature distribution shown in FIG. 14A and temperature distribution of the second area (Cal_2) of the temperature distribution shown in FIG. 14B.

Description will be made on a trouble caused by the amount of light receiving from the two left and right light sources being different between the first area (Cal_1) that is not affected by the shadows of the treatment device 5 and the second area (Cal_2) that is affected by the shadows, using drawings. FIG. 14A shows temperature distribution on a certain surface of the temperature-sensitive phantom 10 at the time of performing calibration using only the color-temperature conversion table 17 based on temperatures of the evaluation temperature-sensitive phantom 10 and hues of the first area (Cal_1). FIG. 14B shows temperature distribution on the same surface of the temperature-sensitive phantom 10 as FIG. 14A at the time of performing calibration using only the color-temperature conversion table 17 based on the temperatures of the temperature-sensitive phantom 10 and hues of the second area (Cal_2). FIG. 14C shows a result of combining temperature distribution of the first area (Cal_1) of the temperature distribution shown in FIG. 14A and temperature distribution of the second area (Cal_2) of the temperature distribution shown in FIG. 14B.

When calibration is performed using only the color-temperature conversion table 17 based on the temperatures of the temperature-sensitive phantom 10 and the hues of the first area (Cal_1), calibration is relatively appropriately performed, and temperature conversion is performed for the first area (Cal_1), but the temperatures are displayed higher or lower than normal temperatures for the second area (Cal_2) as shown in FIG. 14A. In comparison, when calibration is performed using only the color-temperature conversion table 17 based on the temperatures of the temperature-sensitive phantom 10 and the hues of the second area (Cal_2), calibration is relatively appropriately performed for the second area (Cal_2), but, for the first area (Cal_1), the temperatures tend to be converted low and displayed as shown in FIG. 14B. Therefore, a first relationship between the temperatures of the temperature-sensitive phantom 10 and the hues of the first area (Cal_1) is used for calibration of table values corresponding to the first area (Cal_1) in the color-temperature conversion table 17, and a second relationship between the temperatures of the temperature-sensitive phantom 10 and the hues of the second area (Cal_2) is used for calibration of table values corresponding to the second area (Cal_2) in the color-temperature conversion table 17 to form temperature distribution for each. Then, by combining the temperature distributions, the temperature distribution shown in FIG. 14C is obtained.

Third Embodiment

Figure 15:
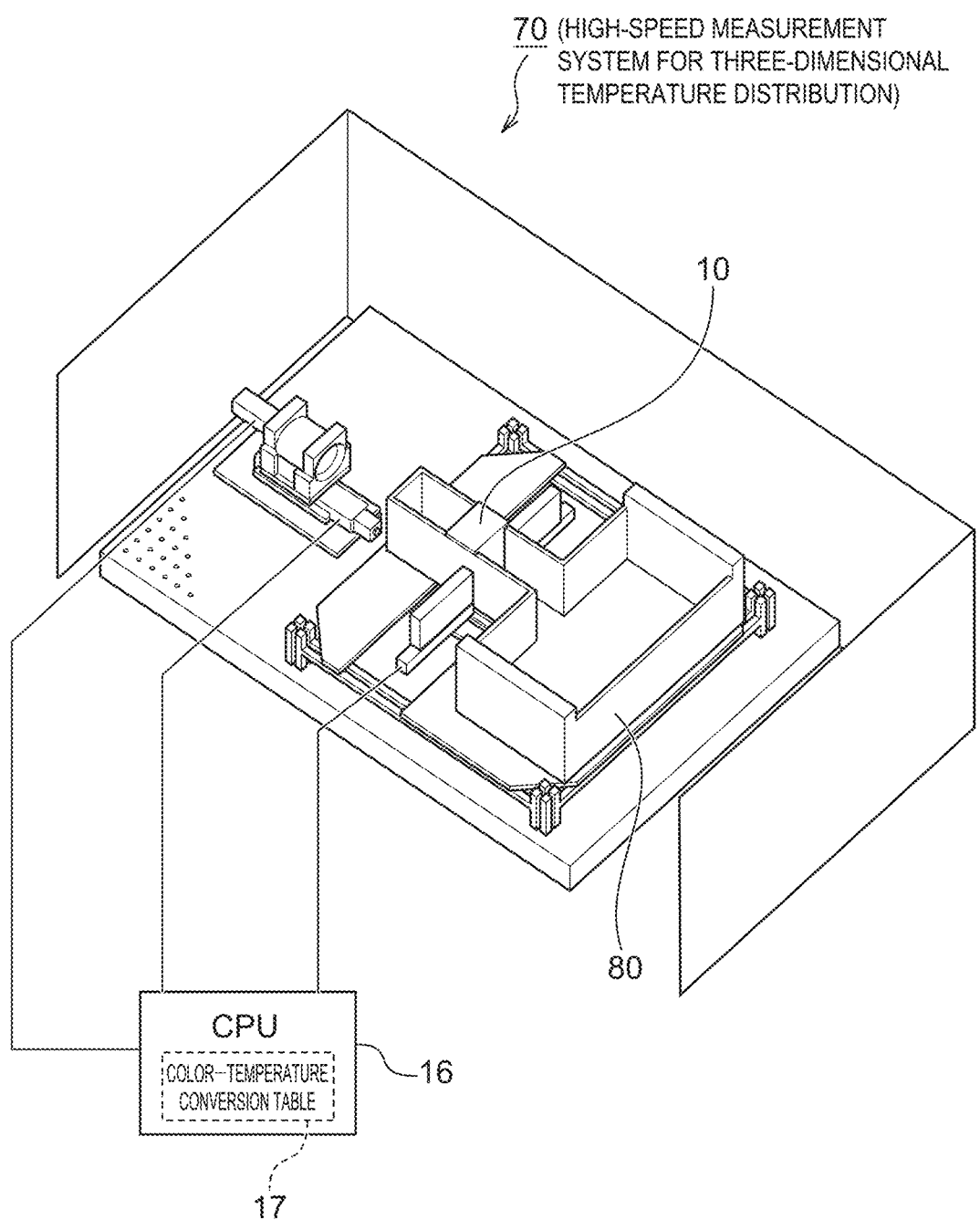
FIG. 15 is a schematic diagram showing a configuration of a three-dimensional temperature distribution high-speed measurement system according to a third embodiment.

FIG. 15 is a schematic diagram showing a configuration of a three-dimensional temperature distribution high-speed measurement system 70 according to a third embodiment. As for components that are the same as or similar to those of the three-dimensional temperature distribution high-speed measurement system 1 or 50 according to the first or second embodiment, the same or similar reference signs will be given, and description of the components will be omitted. The three-dimensional temperature distribution high-speed measurement system 50 according to the second embodiment is configured so that the color-temperature conversion table 17 is calibrated based on temperatures measured by the thermocouple 60 and hues of taken images. In comparison, the three-dimensional temperature distribution high-speed measurement system 70 according to the third embodiment described below is different in that a water tank 80 capable of adjusting water temperature is provided, and the color-temperature conversion table 17 is created based on water temperatures in the water tank 80 and hues of images of the temperature-sensitive phantom 10. As for a light source of the three-dimensional temperature distribution high-speed measurement system 70 according to the third embodiment, the light source of the three-dimensional temperature distribution high-speed measurement system 1 according to the first embodiment may be used, or the light sources of the three-dimensional temperature distribution high-speed measurement system 50 according to the second embodiment (radiating light from both sides of the temperature-sensitive phantom 10) may be used.

The three-dimensional temperature distribution high-speed measurement system 70 according to the third embodiment shown in FIG. 15 includes the water tank 80 capable of making an adjustment to a predetermined temperature by a heater (not shown), and the water tank 80 accommodates the temperature-sensitive phantom 10 inside. The movement mechanism control/information processing unit 16 controls water temperature inside the water tank 80 and acquires hues of images of the temperature-sensitive phantom 10 in association with water temperatures inside the water tank 80. Thereby, the movement mechanism control/information processing unit 16 acquires the color-temperature conversion table 17 based on the temperatures and the hues. As for an evaluation method, display of data, and the like are almost similar to those of the first and second embodiments. Since only the calibration method is different, the calibration method in the three-dimensional temperature distribution high-speed measurement system 70 according to the third embodiment will be described below.

Calibration Method

Figure 16:
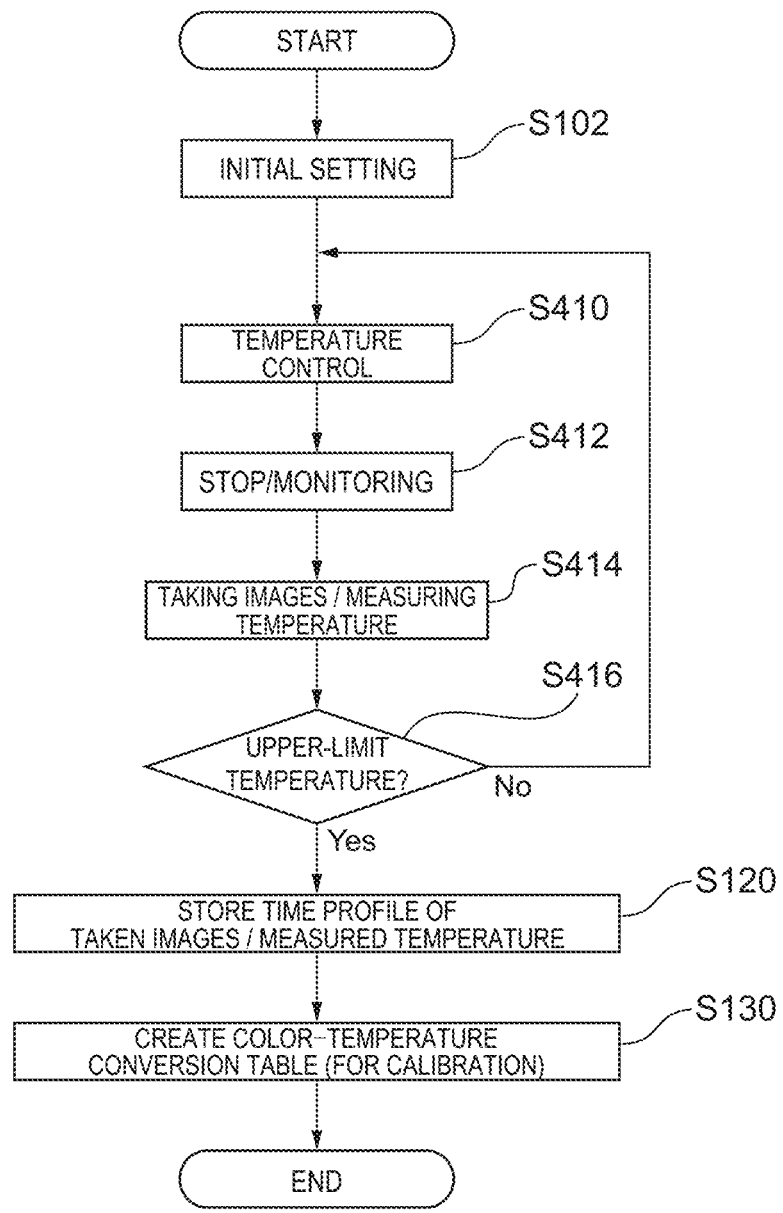
FIG. 16 is a flowchart of a calibration method executed in the three-dimensional temperature distribution high-speed measurement system according to the third embodiment.

The calibration method executed in the three-dimensional temperature distribution high-speed measurement system 70 according to the third embodiment will be described below. FIG. 16 is a flowchart of a method for acquiring the color-temperature conversion table 17 executed in the three-dimensional temperature distribution high-speed measurement system 70. Since focusing is the same as the focusing at the initial setting in the three-dimensional temperature distribution high-speed measurement systems 1 and 50 of the first and second embodiments, description thereof will be omitted. At initial setting, one phantom hue measurement point is specified in the case of using the light source of the first embodiment, and two positions (the first area Cal_1 and the second area Cal_2 described before) are specified in the case of using the light sources of the second embodiment.

When the initial setting is completed, the movement mechanism control/information processing unit 16 heats the water in the water tank 80 to a lower-limit temperature of a temperature-sensitive area by the heater (not shown) (a temperature control process: S410). When the lower-limit temperature of the temperature-sensitive area is reached, the movement mechanism control/information processing unit 16 stops the heater and waits until the temperature of the temperature-sensitive phantom 10 is stabilized (a stop process: S412). When the temperature of the whole temperature-sensitive phantom 10 is stabilized, the image taking device 14 takes an image of the whole temperature-sensitive phantom 10, and water temperature at that time-temperature-sensitive phantom temperature is measured (an image taking/temperature measurement process: S414).

Then, the water in the water tank 80 is heated by a predetermined temperature width (a temperature control process: S410). Similarly to the above, when the temperature of the whole temperature-sensitive phantom 10 is stabilized (a stop process: S412), an image of the whole temperature-sensitive phantom 10 is taken, and temperature is measured (an image taking/temperature measurement process: S414). The phantom hue-temperature relationship is acquired until an upper-limit temperature of the temperature-sensitive area is reached, and, when the upper-limit temperature is reached, a time profile of the taken images and temperature measurements are stored (a storage process: S120). After that, creation of the color-temperature conversion table is performed using the method described before (a calibration process: S130). At S130, one kind of color-temperature change table is created in the case of using the light source of the first embodiment, and two kinds of color-temperature change tables (for the first area Cal_1 and the second area Cal_2 described before) are created in the case of using the light sources of the second embodiment.

Though an example of acquiring a temperature distribution image in a process of the temperature of the temperature-sensitive phantom 10 rising has been described in the above description, it is possible to acquire the temperature distribution image in a process of the temperature-sensitive phantom 10 naturally cooling down.

Evaluation Method

A flowchart of the evaluation method in the third embodiment is also almost similar to that of the first embodiment (FIG. 8). As described before, the number of color-temperature conversion tables differs according to the type of light source used. In addition, it is the same as the first and second embodiments that it is possible to output temperature distribution of the temperature-sensitive phantom 10 and temporal temperature-distribution change in response to a request by the user (the input means is not shown).

An advantage of the third embodiment is that it is not necessary to separately prepare a temperature-sensitive phantom for calibration. In the first and second embodiments, since a temperature-sensitive phantom is invaded due to a thermocouple, it is necessary to separately prepare a temperature-sensitive phantom for evaluation. In the third embodiment, however, it is possible to, after calibration with a temperature-sensitive phantom ends, transition to evaluation without the necessity of exchanging the temperature-sensitive phantom.

The invention claimed is:

1. A system for quantitatively evaluating a treatment device capable of radiating ultrasound for heating human tissue, the system comprising:

simulated tissue having a property that hue changes according to temperature in a particular temperature-sensitive area, the simulated tissue simulating temperature change of human tissue at time of the human tissue receiving the ultrasound from the treatment device;
a light source radiating planar light to the simulated tissue;
an image taking device taking cross-sectional color images of light irradiation surfaces of the simulated tissue;
movement mechanisms causing the light source and the image taking device to relatively move in a photographing axis direction of the image taking device relative to the simulated tissue;
a color-temperature conversion table for converting from hues of the images of the simulated tissue to temperatures; and
movement mechanism control/information processing means for controlling the movement mechanisms so that the light source and the image taking device move in a state of keeping a distance between the light irradiation surface and the image taking device constant, and further acquiring temperature distributions of the simulated tissue from the hues at positions on the taken images of the simulated tissue, using the color-temperature conversion table.

2. The system according to claim 1, wherein the movement mechanism control/information processing means acquires the temperature distributions in the photographing axis direction of the simulated tissue, from images taken under image taking conditions using the color-temperature conversion table and outputs three-dimensional temperature distribution from the temperature distributions of the simulated tissue.

3. The system according to claim 1, further comprising image holding means for holding the acquired temperature distributions of the simulated tissue as images, wherein
the movement mechanism control/information processing means outputs temporal temperature-distribution change of the simulated tissue based on the held temperature distribution images.

4. The system according to claim 1, further comprising a thermocouple arranged in the simulated tissue, wherein
the movement mechanism control/information processing means creates the color-temperature conversion table based on measured temperatures by the thermocouple and the hues of the images of the simulated tissue.

5. The system according to claim 1, further comprising a water tank capable of adjusting water temperature and accommodating the simulated tissue; wherein
the movement mechanism control/information processing means creates the color-temperature conversion table based on water temperatures of the water tank and hues of images of the simulated tissue accommodated in water in the water tank.

6. The system according to claim 1, wherein the light source surrounds the simulated tissue from 360-degree directions.

7. The system according to claim 1, wherein the light source is arranged at each of symmetrical positions sandwiching the simulated tissue.

8. A method for controlling a system for evaluating a treatment device capable of radiating ultrasound for heating human tissue, the system comprising:
simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;
two light sources radiating planar light to the simulated tissue, the two light sources being arranged at symmetrical positions sandwiching the simulated tissue;
an image taking device taking cross-sectional color images of light irradiation surfaces of the simulated tissue;
movement mechanisms causing the light source and the image taking device to relatively move in a photographing axis direction of the image taking device relative to the simulated tissue;
a color-temperature conversion table for converting from hues of the images of the simulated tissue to temperatures;
movement mechanism control/information processing means for controlling the movement mechanisms so that the light source and the image taking device move in a state of keeping a distance between the light irradiation surface and the image taking device constant, and further acquiring temperature distributions of the simulated tissue from the hues at positions on the taken images of the simulated tissue, using the color-temperature conversion table; and
a first thermocouple arranged in a first area (Cal_1) near the insertion hole in the simulated tissue, the first area (Cal_1) not overlapping with the insertion hole of the simulated tissue when seen from any one of the light sources, and a second thermocouple arranged in a second area (Cal_2) overlapping with the insertion hole of the simulated tissue, and
the treatment device being arranged in the insertion hole of the simulated tissue, wherein
the method comprises causing the movement mechanism control/information processing means to execute:
a heating process of causing the treatment device to radiate the ultrasound to heat the simulated tissue;
a monitoring process of monitoring color change of the heated simulated tissue near the first and second thermocouples through the image taking device;
a stop process of, when the color change of the simulated tissue near the first and second thermocouples is observed, causing the radiation of the ultrasound by the treatment device to stop;
a temperature measurement process of causing each of the first and second thermocouples to measure temperature of the simulated tissue;
a first image taking process of causing the image taking device to take an image of the simulated tissue;
an image division process of dividing the taken image into the first area (Cal_1) and the second area (Cal_2);
a first table calibration process of calibrating table values of the color-temperature conversion table corresponding to the first area (Cal_1) based on the measured temperature and a hue of a position closest to a position of the first thermocouple in the first area (Cal_1); and
a second table calibration process of calibrating table values of the color-temperature conversion table corresponding to the second area (Cal_2), based on the measured temperature and a hue of a position closest to a position of the second thermocouple in the second area (Cal_2).

9. The method according to claim 8, further comprising causing the movement mechanism control/information processing means to, until the simulated tissue reaches a lower-limit temperature of the temperature-sensitive area, repeatedly execute at predetermined time intervals:
a second image taking process of causing the image taking device to take an image of the simulated tissue;
the image division process of dividing the taken image into the first area (Cal_1) and the second area (Cal_2); and
a temperature distribution acquisition process of acquiring temperature distribution from each of the first area (Cal_1) and the second area (Cal_2) of the simulated tissue, using the calibrated color-temperature conversion table.

10. The method according to claim 9, wherein
the system further comprises image holding means for holding the acquired temperature distribution of the simulated tissue as an image;
the temperature distribution acquisition process includes an image holding process of the image holding means holding the acquired temperature distribution; and
the method comprises causing the movement mechanism control/information processing means to execute an output process of outputting temporal temperature-distribution change of the simulated tissue, in response to a request by a system user.

11. A method for controlling a system for evaluating a treatment device capable of radiating ultrasound for cauterizing human tissue, the system comprising:
simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;
two light sources radiating planar light to the simulated tissue, the two light sources being arranged at symmetrical positions sandwiching the simulated tissue;
an image taking device taking cross-sectional color images of light irradiation surfaces of the simulated tissue;
movement mechanisms causing the light sources and the image taking device to relatively move in a photographing axis direction of the image taking device relative to the simulated tissue;
a color-temperature conversion table for converting from hues of the images of the simulated tissue to temperatures;
movement mechanism control/information processing means for controlling the movement mechanisms so that the light sources and the image taking device move in a state of keeping a distance between the light irradiation surface and the image taking device constant, and further acquiring temperature distributions of the simulated tissue from the hues at positions on the taken images of the simulated tissue, using the color-temperature conversion table; and
a water tank capable of adjusting water temperature and accommodating the simulated tissue, wherein
the method comprises causing the movement mechanism control/information processing means to execute:
a temperature control process of controlling water in the water tank to be at a predetermined temperature;
an image taking process of causing the image taking device to take an image of the simulated tissue accommodated in the water in the water tank;
an image division process of dividing the taken image into a first area (Cal_1) not overlapping with the insertion hole of the simulated tissue when seen from the light sources and a second area (Cal_2) overlapping with the insertion hole; and
a table calibration process of calibrating the color-temperature conversion table for each of the first area (Cal_1) and the second area (Cal_2) based on the water temperature in the water tank and the hues of the image of the simulated tissue, and
the method further comprises causing the movement mechanism control/information processing means to repeatedly execute the temperature control process, the image taking process, the image division process, and the table calibration process for the entire temperature-sensitive area from a lower-limit temperature to an upper-limit temperature of the temperature-sensitive area of the simulated tissue.

12. The method program to claim 11, wherein
in the system, the treatment system is arranged in the insertion hole of the simulated tissue,
the method comprises causing the movement mechanism control/information processing means to execute:
a heating process of causing the treatment device to radiate the ultrasound to heat the simulated tissue;
an image taking process of causing the image taking device to take an image of the simulated tissue at predetermined time intervals;
the image division process of dividing the taken image into the first area (Cal_1) and the second area (Cal_2); and
a temperature distribution acquisition process of acquiring temperature distribution from each of the first area (Cal_1) and the second area (Cal_2) of the simulated tissue, using the calibrated color-temperature conversion table, and
the method further comprises causing the movement mechanism control/information processing means to repeatedly execute the heating process, the image taking process, the image division process, and the temperature distribution acquisition process for the entire temperature-sensitive area from the lower-limit temperature to the upper-limit temperature of the temperature-sensitive area of the simulated tissue.

13. The method according to claim 12, wherein
the system further comprises image holding means for holding the acquired temperature distributions of the simulated tissue as images,
the temperature distribution acquisition process includes an image holding process of the image holding means holding the acquired temperature distribution, and
the method comprises causing the movement mechanism control/information processing means to execute an output process of outputting temporal temperature-distribution change of the simulated tissue, in response to a request by a system user.

14. A method for calibrating measurement of a system for evaluating a treatment device capable of radiating ultrasound for cauterizing human tissue, the system comprising:
simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;
a light source radiating planar light to the simulated tissue;

an image taking device taking cross-sectional color images of light irradiation surfaces of the simulated tissue;

movement mechanisms causing the light source and the image taking device to relatively move in a photographing axis direction of the image taking device relative to the simulated tissue;

a color-temperature conversion table for converting from hues of the images of the simulated tissue to temperatures;

movement mechanism control/information processing means for controlling the movement mechanisms so that the light source and the image taking device move in a state of keeping a distance between the light irradiation surface and the image taking device constant, and further acquiring temperature distributions of the simulated tissue from taken images of the hues at positions of the simulated tissue using the color-temperature conversion table; and a thermocouple arranged in the simulated tissue, the treatment device being arranged in the insertion hole of the simulated tissue, wherein the method comprises:

a process of the treatment device radiating the ultrasound to heat the whole simulated tissue;

a process of monitoring color change of the heated simulated tissue near the thermocouple;

a process of, when the color change of the simulated tissue near the thermocouple is observed, stopping the radiation of the ultrasound by the treatment device;

a process of the thermocouple measuring temperatures of the simulated tissue;

a process of the image taking device taking the images of the simulated tissue; and a process of calibrating the color-temperature conversion table based on the measured temperatures and hues near the thermocouple on the taken images.

15. A method for calibrating measurement of a system for evaluating a treatment device capable of radiating ultrasound for cauterizing human tissue, the system comprising:

simulated tissue having a property that hue changes according to temperature in a particular temperature-sensitive area and simulating temperature change of human tissue at time of the human tissue receiving the ultrasound from the treatment device, the simulated tissue having an insertion hole where the treatment device can be arranged;

a light source radiating planar light to the simulated tissue;

an image taking device taking cross-sectional color images of light irradiation surfaces of the simulated tissue;

movement mechanisms causing the light source and the image taking device to relatively move in a photographing axis direction of the image taking device relative to the simulated tissue;

a color-temperature conversion table for converting from hues of the images of the simulated tissue to temperatures;

movement mechanism control/information processing means for controlling the movement mechanisms so that the light source and the image taking device move in a state of keeping a distance between the light irradiation surface and the image taking device constant, and further acquiring temperature distributions of the simulated tissue from the hues at positions on the taken images of the simulated tissue, using the color-temperature conversion table; and a water tank capable of adjusting water temperature and accommodating the simulated tissue, wherein the method comprises:

a process of taking an image of the simulated tissue accommodated in water in the water tank controlled to be at a predetermined temperature; and a process of changing the water temperature in the water tank for the entire temperature-sensitive area from a lower-limit temperature to an upper-limit temperature of the simulated tissue to repeat the process of taking an image, and calibrating the color-temperature conversion table for the entire temperature-sensitive area based on water temperatures in the water tank and hues of taken images of the simulated tissue.

* * * * *